United States Patent [19]
Friedman

[11] Patent Number: 6,149,929
[45] Date of Patent: Nov. 21, 2000

[54] GREEN WATER INHIBITOR-GWI

[76] Inventor: Robert S. Friedman, 137 Fairfield Cir., Ventura, Calif. 93003

[21] Appl. No.: 09/232,781

[22] Filed: Jan. 19, 1999

[51] Int. Cl.[7] .......................... A61K 35/78; A01N 61/00; A01N 63/02; A01N 31/08; C12N 1/20

[52] U.S. Cl. ...................... 424/405; 424/195.1; 504/161; 504/150; 504/117; 504/118; 435/243

[58] Field of Search ................................. 424/405, 195.1; 504/161, 117, 118, 353, 150; 435/243

[56] References Cited

U.S. PATENT DOCUMENTS

| | | |
|---|---|---|
| 4,319,041 | 3/1982 | Goff . |
| 4,647,537 | 3/1987 | Shigemitsu . |
| 4,735,014 | 4/1988 | Weber . |
| 5,292,410 | 3/1994 | Sweeney . |

FOREIGN PATENT DOCUMENTS

| | | |
|---|---|---|
| 405007482 | 1/1993 | Japan . |

OTHER PUBLICATIONS

Flachowsky et al., Effect of NaOh and $H_2O_2$ on the Degradability of Straw in Ruminants, Arch. Animal Nutr., 38(10), 1988, pp. 955–984.

*Primary Examiner*—Edward J. Webman

[57] ABSTRACT

A composition for effective algae control comprising bacteria and humic acid made by extracting the liquid from barley straw soaked in water for a period of time.

2 Claims, No Drawings

GREEN WATER INHIBITOR-GWI

PRIOR ART

Two British scientists discovered that barley straw was an effective algae control. They recommended placing a bale in a half acre of water in fish farms.

This process involves hauling cumbersome bales to farms, tethering them to heavy weights, and waiting six to eight weeks for secretions to seep into the water. Some parts of the USA don't grow barley straw nor do some foreign countries.

My GWI process brings much quicker and more positive results with less inconvenience and costs. Packaged in quarts, gallons and 55-gallon drums.

My GWI process makes the finished ready-to-use product available to the hobbyist, aquaculturists, lake and reservoir owners, eliminating the need to buy straw bales.

It can readily be seen that time, convenience and economy will be the benifits of my processing and distributing invention, "GWI" Green Water Inhibitor.

Methods of application: Spraying from a boat or the banks of lakes. Airplane spraying of large lakes. Results are evident in some cases, within hours and other situations, one to four days.

The straw bales require weeks before results are evident.

If there is no moving current or water turbulence, the straw bales can not disperse enough of their secretions to accomplish their algae control for very long periods as more algae is being generated daily.

Thus it can be readily seen that the efficacy, convenience and economy lies in the utilization of my invention as opposed to the methodology recommended by the scientists.

One aspect of the invention is a composition comprising humic acid and bacteria in 25 gallons of water made by a process comprising soaking 5 pounds of barley straw in 25 gallons of water for 48 hours and extracting the resulting liquid from the straw.

The process can further include adding heat and oxygen to the mixture of barley straw and water. The process can optionally further include the addition of dried select microbial species to the resulting liquid to enhance the viability of the product and increase the bacterial population. The time required to soak the barley straw can vary, as can the quantity of water that it is soaked in. None of the embodiments of the invention are necessarily limited to the amounts described herein.

What is claimed is:

1. A composition comprising humic acid and bacteria in about 25 gallons of water make by the process comprising soaking about 5 pounds of barley straw in about 25 gallons of water for about 48 hours and extracting the resulting liquid from the straw.

2. A process for making a composition comprising humic acid and bacteria comprising the a first step of soaking about 5 pounds of barley straw in about 25 gallons of water for about 48 hours and a second step of extracting the resultant liquid from the straw.

* * * * *